United States Patent [19]

Kirk et al.

[11] Patent Number: 5,541,092
[45] Date of Patent: Jul. 30, 1996

[54] PROCESS FOR PREPARING PEROXYCARBOXYLIC ACIDS USING LIPASE IN A NON-AQUEOUS MEDIUM

[75] Inventors: Ole Kirk, Copenhagen N, Denmark; Frederik Björkling, Helsingborg, Sweden; Sven Erik Godtfredsen, Vaerloese, Denmark

[73] Assignee: Novo Nordisk A/S, Bagsvaerd, Denmark

[21] Appl. No.: 204,693

[22] Filed: Mar. 1, 1994

Related U.S. Application Data

[63] Continuation of Ser. No. 60,191, May 7, 1993, abandoned, which is a continuation of Ser. No. 836,317, Feb. 28, 1992, abandoned.

[30] Foreign Application Priority Data

Sep. 12, 1989 [DK] Denmark .................................. 4503/89
Jul. 20, 1990 [DK] Denmark .................................. 1737/90

[51] Int. Cl.⁶ .............................. C12P 7/00; C12P 13/00; C12P 11/00
[52] U.S. Cl. .......................... 435/132; 435/128; 435/130
[58] Field of Search .................................. 435/130, 127, 435/128, 132, 130

[56] References Cited

FOREIGN PATENT DOCUMENTS

| | | |
|---|---|---|
| 45861/72 | 2/1974 | Australia . |
| 253487 | 1/1988 | European Pat. Off. . |
| 268456 | 5/1988 | European Pat. Off. . |
| 0310952 | 4/1989 | European Pat. Off. . |
| 1401312 | 7/1925 | United Kingdom . |
| 9114783 | 10/1991 | WIPO . |

OTHER PUBLICATIONS

Ullmann's Encyclopedia of Industrial Chemistry, vol. A19, pp. 206–210.

Zacks et al, Proc. Natl Acad Sci 82:3192–96 (1985).

*Primary Examiner*—Michael G. Wityshyn
*Assistant Examiner*—Sandra Saucier
*Attorney, Agent, or Firm*—Steve T. Zelson, Esq.; Elias J. Lambiris, Esq.

[57] ABSTRACT

A process for the preparation of a peroxycarboxylic acid of general formula (I), wherein R is an organic residue, in particular a linear or branched alkyled group, an aryl group or an alkyl aryl group each of which is optionally substituted with one or more groups, the process comprising treating a carboxylic acid of the general formula R—COOH, wherein R has the meaning indicated above, with hydrogen peroxide or a precursor thereof in the presence of an enzyme catalyst is described. The enzyme catalyst is preferably a hydrolase, such as a protease or a lipase. Also, a process for the oxidation of organic compounds with the peroxycarboxylic acids thus prepared is described.

19 Claims, 1 Drawing Sheet

PROCESS FOR PREPARING PEROXYCARBOXYLIC ACIDS USING LIPASE IN A NON-AQUEOUS MEDIUM

This application is a continuation application of application Ser. No. 08/060,191, filed May 7, 1993 which is now abandoned, which is a continuation application of application Ser. No. 07/836,317, filed Feb. 28, 1992, now abandoned, the contents of which are incorporated herein by reference.

FIELD OF INVENTION

The present invention relates to a novel process for the preparation of peroxycarboxylic acids. Also, the present invention relates to a process for the oxidation of organic compounds with the peroxycarboxylic acids thus prepared.

BACKGROUND OF THE INVENTION

Peroxycarboxylic acids are commonly employed as oxidizing reagents in the field of organic synthesis for the production of organic chemicals. A wide variety of organic molecules may be oxidized by means of these reagents which, for instance, are useful for the preparation of epoxides from unsaturated hydrocarbons. The various uses of peroxycarboxylic acids are exhaustively described in the art, e.g. in *Comprehensive Organic Chemistry* edited by Barton and Ollis, Pergamon Press, 1979. Some peroxycarboxylic acids such as meta-chloro-peroxybenzoic acid have become commercially available as a result of their wide applicability.

Even though some peroxycarboxylic acids are useful and commercially available reagents their use is limited because of their relatively high cost and the risks (in particular the explosion hazard) involved in handling the reagents, especially when this is done on a large scale. Accordingly, there is a need for improved methods of preparing peroxycarboxylic acids as well as for methods which make it safer to use them in organic synthesis.

DISCLOSURE OF THE INVENTION

It has surprisingly been found that peroxycarboxylic acids may be generated by treating carboxylic acids with hydrogen peroxide in the presence of an enzyme. This method of preparing peroxycarboxylic acids presents a safe and economically viable approach for the preparation of these highly useful reagents. It has also been found that enzymatic synthesis of peroxycarboxylic acids and oxidation of organic chemicals by means of peroxycarboxylic acids may be carried out simultaneously.

Accordingly, the present invention relates to a process for the preparation of a peroxycarboxylic acid of the general formula (I)

$$R-C\begin{matrix}\diagup\hspace{-2pt}\diagup O\\ \diagdown O-OH\end{matrix} \quad (I)$$

wherein R is an organic residue, in particular a linear or branched, saturated or unsaturated alkyl group, an aryl group or an alkyl aryl group each of which may optionally be substituted with one or more hydroxy, thio, alkyloxy, alkoxy, nitro, oxy, keto, oxo, halo or carboxy groups, the process comprising treating a carboxylic acid of the general formula (II)

$$R-COOH \quad (II)$$

wherein R has the meaning indicated above, with hydrogen peroxide or a precursor thereof in the presence of an enzyme catalyst.

The process of the invention may be summarized as indicated in Reaction Scheme (A):

$$R-C\begin{matrix}\diagup\hspace{-2pt}\diagup O\\ \diagdown OH\end{matrix} \xrightarrow{\text{Enzyme}} R-C\begin{matrix}\diagup\hspace{-2pt}\diagup O\\ \diagdown OOH\end{matrix} \quad (A)$$
$$(II) \qquad\qquad (I)$$
$$H_2O_2 \quad H_2O$$
$$H_2O_2 \text{ precursor}$$

In Reaction Scheme (A), R is as defined above. In particular, R may be alkyl with 1–30 carbon atoms, in particular linear alkyl with 1–8 carbon atoms, or optionally substituted phenyl. If the carboxylic acid substrate (II) is an optically active carboxylic acid, one may employ a racemate or either of the enantiomer forms of the carboxylic acid substrate (II) in the process of the invention.

The enzyme catalyst employed in the process of the invention is preferably a hydrolytic enzyme such as a protease or a lipase. The suitability of a given enzyme for use in the present process may easily be tested by exposing a carboxylic acid substrate to hydrogen peroxide or a hydrogen peroxide precursor in the presence of the enzyme and by monitoring the generation of peroxycarboxylic acid from the reaction. The enzyme may be used as such, but it may also be chemically modified or immobilised in order to enhance its stability and its activity towards the substrate in question.

Lipases which may be employed in the present process may be microbial lipases produced, for instance, by strains of Aspergillus, Enterobacterium, Chromobacterium, Geotrichum or Penicillium. Preferred lipases for use according to the invention are those produced by species of Mucor, Humicola, Pseudomonas or Candida.

Particularly preferred lipases are those produced by the following strains of microorganisms, all of which have been deposited in the Deutsche Sammlung von Mikroorganismen in accordance with the provisions of the Budapest Treaty on the International Recognition of the Deposit of Microorganisms for the purposes of Patent Procedure:

*Candida antarctica*, deposited on 29 Sep. 1986, with the number DSM 3855, and on 8 December 1986, with the numbers DSM 3908 and DSM 3909.

*Pseudomonas cepacia*, deposited on 30 Jan. 1987, with the number 3959.

*Humicola lanuginosa*, deposited on 13 Aug. 1986 and 4 May, 1987 with the deposit numbers 3819 and 4109, respectively.

*Humicola brevispora*, deposited on 4 May 1987, with the deposit number DSM 4110,

*Humicola brevis var. thermoidea*, deposited on 4 May 1987, with the deposit number DSM 4111, and

*Humicola insolens*, deposited on 1 Oct. 1981, with the deposit number DSM 1800.

Currently preferred lipases are those produced by *Candida antarctica*, DSM 3855, DSM 3908 and DSM 3909. These enzymes may be produced by the process disclosed in WO 88/02775. Briefly, the Candida strains in question may be cultivated under aerobic conditions in a nutrient medium containing assimilable carbon and nitrogen sources as well as essential minerals, trace elements etc., the medium being composed according to established practice. After cultivation, liquid enzyme concentrates may be prepared by removing insoluble materials, e.g. by filtration or centrifugation, after which the culture broth may be concentrated by evaporation or reverse osmosis. Solid enzyme preparations may be prepared from the concentrate by precipitation with salts or water-miscible solvents, e.g. ethanol, or by drying such as spray-drying in accordance with well-known methods.

Additional lipases may be obtained from the following strains which are publicly available without restriction from the Centraalbureau voor Schimmelculturen (CBS), American Type Culture Collection (ATCC), Agricultural Research Culture Collection (NRRL) and Institute of Fermentation, Osaka (IFO) with the following deposit numbers: *Candida antarctica*, ATCC 34888, ATCC 28323, CBS 6821 and NRRL Y-7954; *Candida tsukubaensis*, ATCC 24555; *Candida auricularia*, ATTC 24121; *Candida humicola*, ATCC 14438, ATCC 9949, and IFO 1527; and *Candida foliarum*, and ATCC. 18820.

It is known to produce lipase by recombinant DNA techniques, cf. for instance EP 238 023. Recombinant lipases may also be employed for the present purpose.

When employed in the process of the invention, the enzyme may be in a soluble state. It is, however, preferred to immobilize the enzyme in order to facilitate the recovery of the peroxycarboxylic acids produced by the present process. Immobilization procedures are well known (cf. for instance K. Mosbach, ed., "Immobilized Enzymes", *Methods in Enzymology* 44, Academic Press, New York, 1976) and include cross-linking of cell homogenates, covalent coupling to insoluble organic or inorganic supports, entrapment in gels and adsorption to ion exchange resins or other adsorbent materials. Coating on a particulate support may also be employed (cf. for instance A. R. Macrae and R. C. Hammond, *Biotechnology and Genetic Engineering Reviews* 3, 1985, p. 193. Suitable support materials for the immobilized enzyme are, for instance, plastics (e.g. polypropylene, polystyrene, polyvinylchloride, polyurethane, latex, nylon, teflon, dacron, polyvinylacetate, polyvinylalcohol or any suitable copolymer thereof), polysaccharides (e.g. agarose or dextran), ion exchange resins (both cation and anion exchange resins), silicon polymers (e.g. siloxane) or silicates (e.g. glass).

It is preferred to immobilize the enzyme on an ion exchange resin by adsorbing the enzyme to the resin or by cross-linking it to the resin by means of glutaraldehyde or another cross-linking agent in a manner known per se. A particularly preferred resin is a weakly basic anion exchange resin which may be a polystyrene-, acrylic- or phenol-formaldehyde-type resin. Examples of commercially available polyacrylic-type resins are Lewatit E 1999/85 (registered trademark of Bayer, Federal Republic of Germany) and Duolite ES-568 (registered trademark of Rohm & Haas, FRG). Immobilization of enzymes to this type of resin may be carried out according to EP 140 542. Immobilization to phenyl-formaldehyde-type resins may be done according to DK 85/878. An example of a commercially available acrylic-type resin is Lewatit E2001/85 (registered trademark of Bayer, FRG).

Another convenient material for immobilizing enzymes is an inorganic support, such as a silicate. The enzyme may be attached to the support by adsorption or by covalent coupling, eg. as described in K. Mosbach, ed., *op.cit.*

The process according to the method of the invention may be carried out in the carboxylic acid substrate itself (which in this case also acts as a solvent) or in solvents such as water, aqueous buffer solutions or organic solvents. Some preferred organic solvents are hydrocarbons such as hexane, cyclohexane, heptane, benzene and toluene, methylene chloride and hexachloroethane, or acetonitrile, dimethylformamide, dioxane and tetrahydrofuran. It is preferred to employ solvents in which the substrate and products of the reaction are highly soluble and in which the enzyme maintains a good stability and activity.

If an organic substance e.g. an alkene is to be oxidized in situ by the Peroxycarboxylic acid being formed, this substance may advantageously be used as the solvent.

The temperature at which the reaction of the carboxylic acid (II) takes place is not critical, but is conveniently in the range of about 20°–100° C., such as about 30°–80° C.

The hydrogen peroxide employed according to the process of the invention may be added as such to the reaction mixture either at the beginning of the reaction or at a desired rate in the course of the reaction. Alternatively, it is possible to employ a precursor of hydrogen peroxide such precursors being compounds which give rise to the formation of hydrogen peroxide in situ, such as percarbonates or perborates.

The water generated in the course of the process according to the invention may, if desired, be removed by methods known in the art such as by distillation, exposure to dessicants etc.

As indicated above, it has surprisingly been found that the process of the present invention may be carried out concomitantly with oxidation of an organic compound susceptible to oxidation with peroxycarboxylic acids as indicated in Reaction Scheme (B) below:

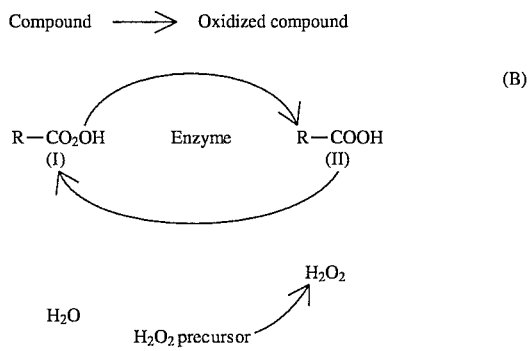

In Reaction Scheme (B) the "compound" may be any compound susceptible to peroxycarboxylic acid oxidation, e.g. an unsaturated hydrocarbon or a sulphur-containing organic molecule, while "R", "Enzyme" and "$H_2O_2$-precursor" have the meanings indicated above.

The process of the invention shown in Reaction Scheme (B) above may be carried out using substantially equimolar amounts of the "compound" and the carboxylic acid substrate (II). If desired, however, the process may be carried out using less than equimolar amounts of the carboxylic acid (II) since this compound will be regenerated in the course of the reaction as indicated in Reaction Scheme (B).

The process shown in Reaction Scheme (B) makes it unnecessary to transport and handle large quantities of peroxycarboxylic acids so that the hazards involved in using these oxidants are greatly reduced.

Furthermore, as indicated above, the carboxylic acid (II) may be prochiral or chiral and, in such instances, employed as a racemate or as either of its optically active stereoisomers. In cases, where the "compound" is prochiral or chiral, the carboxylic acid substrate (II) and the enzyme may be so selected that the "oxidized compound" is generated in a desired optically active form or as a racemate. The process of the invention may thus be employed for the synthesis of optically active compounds.

The process shown in Reaction Scheme (B) has for instance been found to be advantageous in the preparation of epoxides from alkenes.

Figure 1:
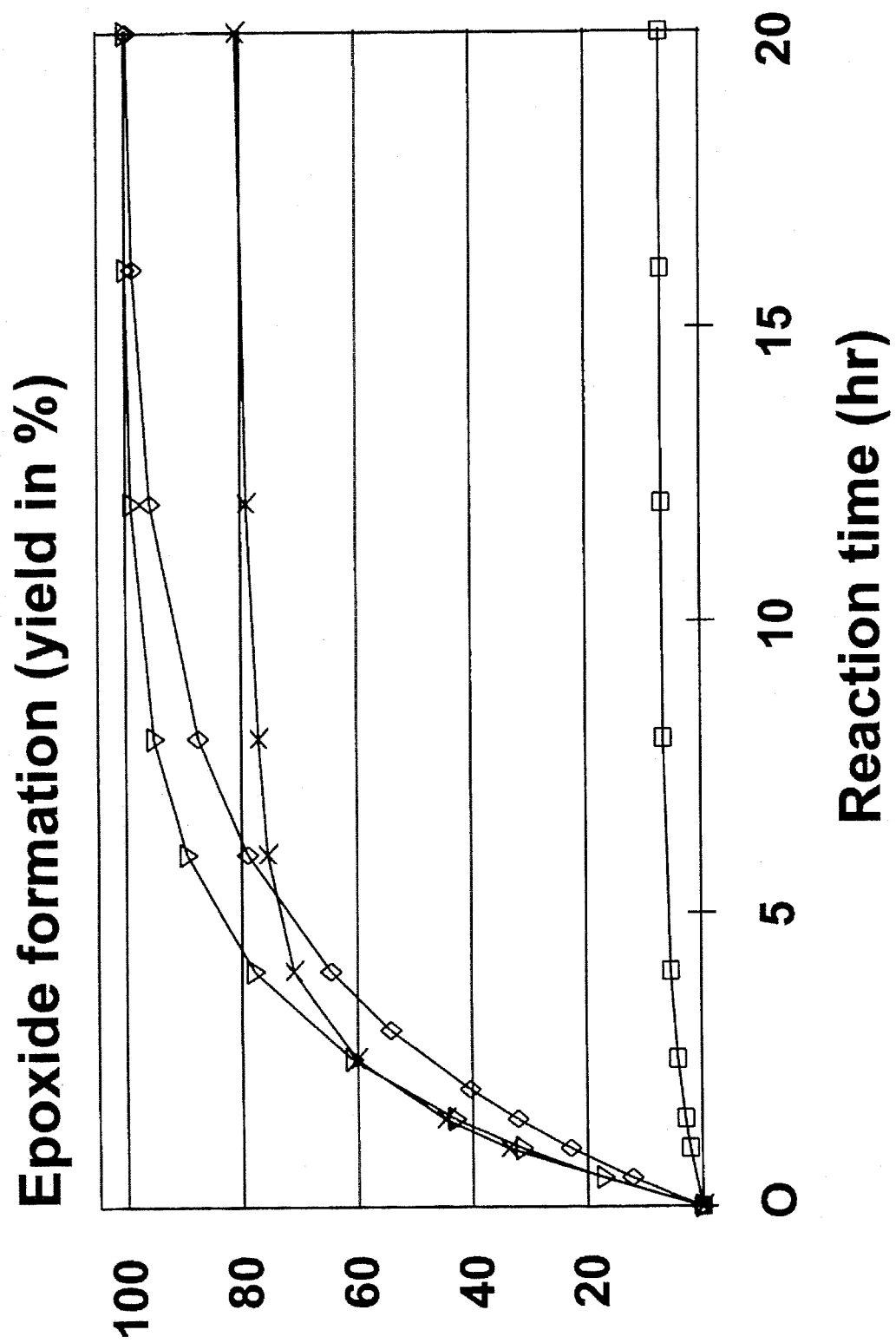
FIG. 1 is a graph of the rate of epoxide formation from various alkanes using a percarboxylic acid formed by the reaction of octanoic acid and hydrogen peroxide using lipase from *C. antarctica*. ◊ is cyclohexane, X is 3-ethyl-2-pentene, ∇ is tetramethylene and □ is 1-octene.

The process of the invention is further illustrated in the following non-limiting examples.

GENERAL PROCEDURES

Peroxycarboxylic acid references were prepared according to W. E. Parker, C. Ricciuti, C. L. Ogg and D. Swern, *J. Am. Chem. Soc.* 77, 4037 (1955). Peroxycarboxylic acid production was monitored by means of HPLC (Merck LiChrosorb RP-18 column, MeOH/$H_2O$/HCOOH; 70/30/0.1, and UV-detector). Reactions were monitored by means of capillary gas chromatography.

EXAMPLE 1

To a stirred solution of octanoic acid (720 mg, 5 mmol) in hexane (50 ml) was added immobilized lipase derived from *Candida antarctica* (1 g, prepared according to examples 1 and 19 of WO 88/02775) and hydrogen peroxide (170 mg, 5 mmol, added as 510 µl 30% solution). After the reaction mixture had been refluxed for 30 min, HPLC analysis showed a peroxyoctanoic acid concentration of 43 mM (43% conversion).

EXAMPLE 2

Octanoic acid was oxidized as described in example 1 with the exception that acetonitrile was used as the solvent. After 30 min, 15 mM peroxyoctanoic acid was detected.

EXAMPLE 3

Example 1 was repeated in the presence of either 10 mM styrene or 10 mM 1,2-epoxyethylbenzene. In both cases, a peroxycarboxylic acid production which was comparable to that of example 1 was observed. Thus the enzyme did not appear to be inhibited by either of these compounds.

EXAMPLE 4

Preparation of styrene oxide:

To a stirred suspension (at room temperature) of immobilized *C. antarctica* lipase (370 mg, according to example 1) in styrene (4.15 ml, 36.1 mmol) containing myristic acid (823 mg, 3.6 mmol) hydrogen peroxide (3 ml, 52.5 mmol) was added in six equal portions after 0, 0.5, 1.0, 1.5, 2.0 and 3.0 hours. After 1.5 hours 16.5% styrene oxide was formed as determined by gas chromatography.

EXAMPLE 5

Peroxycarboxylic acids were prepared from various carboxylic acids (see Table 1) as follows:

To a solution of carboxylic acid (630 mM, 3.15 mmol) in toluene (5 ml) was added immobilized *C. antarctica* lipase (100 mg, as described in example 1) and hydrogen peroxide (255 µl, 60% (w/v), 4.45 mmol), with stirring. The reaction was allowed to proceed at room temperature for 120 minutes after which the yield of peroxycarboxylic acid was determined by RP-18 HPLC. The results are shown in Table 1 below.

TABLE 1

| Carboxylic acid | mM peroxycarboxylic acid |
| --- | --- |
| Hexanoic acid | 228 |
| Octanoic acid | 236* |
| Decanoic acid | 249 |
| Dodecanoic acid | 270 |
| Tetradecanoic acid | 277 |
| Hexadecanoic acid | 271 |
| Octadecanoic acid | 170 |

*In this case, xylene was used as the solvent due to interference by toluene in the assay.

EXAMPLE 6

Epoxides were prepared from various alkenes (cf. Table 2) as follows:

To a stirred suspension of immobilized *C. antarctica* lipase (100 mg, as described in example 1) in a solution of hexane (10 ml), alkene (10mM) and octanoic acid (10mM) was added hydrogen peroxide (25 µl, 0.05 mmol, 60%) at room temperature. The reaction was allowed to proceed for 4 hours after which the yield of epoxide was determined by capillary gas chromatography.

To compare, 10 mM preformed peroxyoctanoic acid (prepared as described in D. Sweern, *Organic Peroxides* 2, Ch. 5, Wiley Interscience, New York, 1971; GB 1 452 730; W. E. Parker et al., *J. Amer. Chem. Soc.* 79, 1957 p. 1929) was added to 10 ml of a 10 mM solution of alkene in hexane. The reaction time in this experiment was also 4 hours. The yield of epoxide was determined as indicated above.

The results are shown in Table 2 below.

TABLE 2

| | % Yield | |
| --- | --- | --- |
| Alkene | Catalytic oxidation | Chemical oxidation |
| Cyclohexene | 2 | 10 |
| 3-Ethyl-2-pentene | 48 | 50 |
| Tetramethylethylene | 99 | 74 |

EXAMPLE 7

Epoxides were prepared from various alkenes (cf. FIG. 1) in a solvent-free medium as follows:

To a stirred suspension of immobilized *C. antarctica* lipase (175 mg, as described in example 1) in alkene (1.75 ml, about 15 mmol) containing octanoic acid (270 µl, 1.7 µmol) was added hydrogen peroxide (235 µl, 60% w/v) at the beginning of the reaction and after 1, 1.5, 2.5 and 4 hours (20 mmol in all). Yields were determined by capillary gas chromatography.

The results are shown in FIG. 1, in which ◊ is cyclohexene, x is 3-ethyl-2-pentene, ∇ is tetramethylethylene, and □ is 1-octene.

EXAMPLE 8

Preparation of hexadecene oxide, method A:

A mechanically stirred suspension of immobilized *C. antarctica* lipase (1 g, according to example 1) in 1-hexadecene (15 ml, ca. 52.4 mmol) containing myristic acid (1.2 g, 5.25 mmol) was heated to 50° C. To this mixture hydrogen peroxide (4.6 ml 60% (w/v)) was added in four equal portions after 0, 1.5, 3 and 4.5 hours (80.5 mmol in all). After 20 hours reaction time 51% hexadecene oxide was formed as determined by gas chromatography.

$^1$H NMR: δ=2.88–2.93 (m, 1H), 2.72–2.76 (dd, 1H), 2.45–2.49 (dd, 1H), 1.5–1.55 (m, 2H), 1.42–1.48 (m, 2H), 1.25–1.32 (m, 22H), 0.89 (t, 3H)

EXAMPLE 9

Preparation of hexadecene oxide, method B:

A mechanically stirred suspension of immobilized *C. antarctica* lipase (1 g, according to example 1) in 1-hexadecene (15 ml, ca. 52.4 mmol) containing myristic acid (3.0 g, 13.1 mmol) was heated to 50° C. To this mixture hydrogen peroxide (4.6 ml 60% (w/v)) was added in four equal portions after 0, 1.5, 3 and 4.5 hours (80.5 mmol in all). After 24 hours reaction time 79.4% hexadecene oxide was formed as determined by gas chromatography.

$^1$H NMR: δ=2.88–2.93 (m, 1H), 2.72–2.76 (dd, 1H), 2.45–2.49 (dd, 1H), 1.5–1.55 (m, 2H), 1.42–1.48 (m, 2H), 1.25–1.32 (m, 22H), 0.89 (t, 3H)

EXAMPLE 10

Preparation of octene oxide, method A:

A mechanically stirred suspension of immobilized *C. antarctica* lipase (100 mg, according to example 1) in toluene (13.5 ml), 1-octene (1.5 ml, 9.54 mmol) and myristic acid (0.22 g, 0.95 mmol) was heated to 50° C. To this mixture hydrogen peroxide (0.8 ml, 60% (w/v)) was added in four equal portions after 0, 1.5, 3 and 4.5 hours (14 mmol in all). After 24 hours 35% octene oxide was formed as determined by gas chromatography.

$^1$H NMR: δ=2.87–2.96 (m, 1H), 2.73–2.78 (dd, 1H), 2.45–2.49 (dd, 1H), 1.5–1.57 (m, 2H), 1.43–1.49 (m, 2H), 1.27–1.39 (m, 6H), 0.9 (t, 3H)

EXAMPLE 11

Preparation of octene oxide, method B:

To a mechanically stirred suspension (50° C.) of immobilized *C. antarctica* lipase (1 g, according to example 1) in 1-octene (15 ml, ca. 95.4 mmol) containing myristic acid (4.356 g, 19.1 mmol) was hydrogen peroxide (8 ml 60% (w/v)) added in four equal portions after 0, 1.5, 3 and 4.5 hours (140 mmol in all). After 6 hours 51% octene oxide was formed as determined by gas chromatography.

$^1$H NMR: δ=2.87–2.96 (m, 1H), 2.73–2.78 (dd, 1H), 2.45–2.49 (dd, 1H), 1.5–1.57 (m, 2H), 1.43–1.49 (m, 2H), 1.27–1.39 (m, 6H), 0.9 (t, 3H)

EXAMPLE 12

Preparation of methylene cyclohexane oxide:

To a stirred suspension (at room temperature) of immobilized *C. antarctica* lipase (24 mg, according to example 1) in toluene (3 ml), methylene cyclohexane (0.24 ml, 2 mmol) and myristic acid (46mg), was hydrogen peroxide (0.175 ml 60% (w/v)) added in five equal portions after 0, 1, 2, 3 and 4 hours. After 24 hours 97% methylene cyclohexane oxide was formed as determined by gas chromatography.

EXAMPLE 13

Preparation of penicillin V sulfoxide:

To a mechanically stirred suspension of immobilized *C. antarctica* lipase (150 mg, according to example 1) in toluene (15 ml) and myristic acid (1 g, 4.6 mmol), was hydrogen peroxide (1.2 ml 60% (w/v), 21 mmol in all) added in four equal portions after 0, 2, 3 and 4 hours. Penicillin V-potassium salt (2.4 g, 6.2 mmol in all) was added in three equal portions after 2, 3 and 4 hours. The yields were determined by HPLC (Column: Supelco RP-18, 5 micro; Mobile phase: Acetonitrile 20% and pH 6.5 Phosphate buffer 80%; Flow: 1 ml/min. UV-detector). Full turnover was reached after 5 hours total reaction time.

EXAMPLE 14

Preparation of didodecane disulfide:

To a suspension of immobilized *C. antarctica* lipase (100 mg, according to example 1) in toluene (5 ml), dodecanthiol (1.18 ml, 4.9 mmol) and myristic acid (1.12 g) was added hydrogen peroxide (0.28 ml 60% (w/v)). Product formed (Tlc, ethylacetate).

EXAMPLE 15

Preparation of δ-valerolactone:

To a stirred suspension (at room temperature) of immobilized *C. antarctica* lipase (100 mg, according to example 1) in toluene (3 ml), cyclopentanone (0.265 ml, 3 mmol) and myristic acid (228 mg), was hydrogen peroxide (0.5 ml 60% w/v, 8.75 mmol) added. After 20 hours 16% δ-valerolactone was formed as determined by gas chromatography.

We claim:

1. A process for preparing a peroxycarboxylic acid of formula I:

comprising reacting a carboxylic acid of the formula R—COOH, wherein R is a straight or branched alkyl group, an aryl group or an alkyl aryl group, each of which is unsubstituted or substituted with one or more hydroxy, thio, alkoxy, nitro, keto, oxo, halo or carboxy groups, with (a) hydrogen peroxide or (b) a precursor of hydrogen peroxide which converts to hydrogen peroxide, in a non-aqueous medium which is selected from the group consisting of an organic solvent and the carboxylic acid, wherein the reaction is catalyzed by a lipase.

2. The process according to claim 1, wherein R is a straight or branched alkyl group.

3. The process according to claim 1, wherein R is a straight or branched alkyl group with 1–30 carbon atoms or a phenyl group which is unsubstituted or substituted.

4. The process according to claim 3, wherein R is a straight or branched alkyl group with 1–8 carbon atoms.

5. The process according to claim 1, wherein R is chiral or prochiral.

6. The process according to claim 1, wherein the non-aqueous medium is an organic solvent selected from the group consisting of hexane, cyclohexane, heptane, benzene, toluene, xylene, methylene chloride, hexachloroethene, acetonitrile, dimethylformamide, dioxane and tetrahydrofuran.

7. The process according to claim 6, wherein the non-aqueous medium is an organic solvent selected from the group consisting of hexane, toluene, xylene, cyclohexane and acetonitrile.

8. The process according to claim 1, wherein the non-aqueous medium is the carboxylic acid.

9. The process according to claim 1, wherein the lipase is a microbial lipase.

10. The process according to claim 1, wherein the lipase is a fungal lipase.

11. The process according to claim 10, wherein the lipase is obtained from a species of Mucor, Aspergillus, Humicola, or Candida.

12. The process according to claim 11, wherein the lipase is obtained from *Candida antarctica*.

13. The process according to claim 12, wherein the lipase is derived from *Candida antarctica*, DSM 3855.

14. The process according to claim 1, wherein the lipase is an immobilized lipase.

15. A process for oxidizing a compound, comprising reacting the compound with (a) a carboxylic acid of the formula R—COOH wherein R is a straight or branched alkyl group, an aryl group or an alkyl aryl group, each of which is unsubstituted or substituted with one or more hydroxy, thio, alkoxy, nitro, keto, oxo, halo or carboxy groups and (b) (i) hydrogen peroxide or (ii) a precursor of hydrogen peroxide which converts to hydrogen peroxide, in an non-aqueous medium which is selected from the group consisting of an organic solvent, the compound and the carboxylic acid, wherein the reaction is catalyzed by a lipase and the compound is an unsaturated hydrocarbon or a sulphur-containing compound.

16. The process according to claim 15, wherein R is a straight or branched alkyl group.

17. The process according to claim 15, wherein the compound to be oxidized is an alkene, penicillin, dodecanthiol or cyclopentanone.

18. The process according to claim 15, wherein the compound to be oxidized is styrene, cyclohexene, 3-ethyl-2-pentene, tetramethylethylene, 1-hexadecene, 1-octene or methylene cyclohexane.

19. The process according to claim 15, wherein the non-aqueous medium is the carboxylic acid or the compound to be oxidized.

* * * * *